United States Patent [19]

Hitzig

[11] Patent Number: 5,658,955

[45] Date of Patent: *Aug. 19, 1997

[54] COMBINED USE OF DOPAMINE AND SEROTONIN AGONISTS IN THE TREATMENT OF IMMUNE DISORDERS

[76] Inventor: Pietr Hitzig, 1319 Blue Mount Rd., Monkton, Md. 21111

[*] Notice: The term of this patent shall not extend beyond the expiration date of Pat. No. 5,502,080.

[21] Appl. No.: 548,314

[22] Filed: Nov. 1, 1995

Related U.S. Application Data

[63] Continuation-in-part of Ser. No. 333,294, Nov. 1, 1994, Pat. No. 5,502,080.

[51] Int. Cl.$^6$ .................................................. A61K 31/135
[52] U.S. Cl. ............................................ 514/654; 514/885
[58] Field of Search ...................................... 514/654, 885

[56] References Cited

PUBLICATIONS

Yatham et al, *Medline Abstract*, No. 95308438, Can. J. Psychiatry, vol. 40, No. 2, pp. 93–96, 1995.

*Primary Examiner*—William R. A. Jarvis
*Attorney, Agent, or Firm*—Nixon & Vanderhye

[57] ABSTRACT

This invention relates to the treatment of the immune disorders fibromyalgia and chronic fatigue syndrome with the combination of therapeutically effective amounts of a serotonin agonist and a dopamine agonist. In addition, a method of improving vector gene therapy with the combination of a serotonin agonist and a dopamine agonist is provided.

10 Claims, No Drawings

COMBINED USE OF DOPAMINE AND SEROTONIN AGONISTS IN THE TREATMENT OF IMMUNE DISORDERS

This application is a continuation-in-part of application of Ser. No. 08/333,294, filed Nov. 1, 1994 now U.S. Pat. No. 5,502,080.

By distinguishing between self and non-self, the immune system mediates the individual's relationship with his or her environment. When the immune system is working properly, it protects the organism from infection; when it is not, the failures of the immune system can result in some of the most challenging and serious diseases encountered in medical practice. The nervous and immune systems have evolved with an exquisite capacity to receive and respond to specific forms of stimulation from the internal or external milieu.

Central nervous system neurotransmitters such as dopamine, serotonin, norepinephrine and prolactin modulate the immune system by both stimulating and inhibiting various aspects of the immune system. Medications that increase central nervous system dopamine and serotonin have been found to act in tandem in controlling addictive cravings and psychoneuroses. Stress, or the state that occurs when the individual has his customary environment disturbed, has been increasing. Its increase is the price mankind is paying for disturbing man's natural environment. Low central nervous system dopamine and serotonin has been found to occur in chronically stressed animals. The addition of dopamine and serotonin results in immune enhancement.

This invention provides therapeutic intervention to disorders of the immune system to restore the patient generally and particularly the immune system to its previous degree of competence. Diverse conditions suited to the procedures of this invention include, but are not limited to, immunodeficiency states such as AIDS and HIV-related diseases, lymphoma, and multiple carcinomas; autoimmune diseases such as psoriasis and inflammatory bowel disease; allergic diseases including rhinitis, asthma, atopic conditions, urticaria, anaphylaxis such as allergen specific, exercise induced and idiopathic, angioedema, and neurodermatitis; and miscellaneous conditions including Crohn's disease, ulcerative colitis, chronic hepatitis B, C or D, Persian Gulf Syndrome, fibromyalgia, chronic fatigue syndrome and dermatologic and arthritis psoriasis.

I have found that the concurrent use of a serotonin agonist and a dopamine agonist, preferably administered at the same time and desirably administered in the same dosage unit (tablet, capsule, solution), provides highly effective, predictable therapy for patients suffering from defects of the immune system.

In addition, dopamine and serotonin play important immodulating roles and thus may have benefit for patients receiving gene therapy. Gene therapy has to date been inhibited or rendered less than effective due to host immune response to the vector(s) used to deliver the desired gene product. This is particularly true with adenoviral vectors. Adenoviral vector administration commonly induces inflammation and antigen-specific cellular and humoral immune responses. This is true with recombinant adenoviral vectors. Currently it is believed that it is unlikely any modifications in vectors will fully eliminate their immunogenicity.

A need exists for a procedure causing only transient immunosuppression, one that minimizes effects on pre-existing immunity. Yang et al describe the use of interleukin-12 or interferon-gamma coadministered with the recombinant adenovirus as diminishing the activation of certain T-cells and allowing efficient readministration of recombinant virus. See *Nature Medicine*, vol. 1, No. 9, September 1995, pp. 890–893.

The present invention includes the administration of a dopamine agonist and a serotonin agonist to reduce the body's immune response to gene therapy vectors, notably adenoviral vectors, and achieve transient immunosuppression to facilitate effective gene therapy.

In a preferred aspect of the invention the serotonin agonist(s) and dopamine agonist(s) are administered in the same unit dosage or pharmaceutical presentation. Current information indicates the use of a serotonergic drug reduces the potentially addictive qualities of dopaminergic drugs. Presentation in a single unit, desirably thoroughly blended together in a pharmaceutically stable combination, renders the potential for the separation of and possible abuse of the dopamine agonist far less likely. This aspect of the invention is particularly important in rendering the product administered unattractive to potential or current amphetamine addicts and thus reduces the potential for abuse.

In another preferred aspect of the invention dopamine agonist is administered in its entirely in the morning and serotonin agonist is administered in two divided doses, one in the morning with the dopamine agonist and the other in the afternoon.

Clinical experiences include the treatment of patients with severe asthma, no asymptomatic; patients with allergic rhinitis, now resolved; patients with psoriasis have experienced marked improvement or complete resolution; patients with AIDS experienced significant improvement of their T cell counts and patients with malignant idiopathic anaphylaxis, now resolved.

A wider variety of serotonin agonists and dopamine agonist may be considered for use in the therapeutic methods and pharmaceutical compositions of the invention. The following is a non-limiting partial listing of products currently approved for use in the United States or other countries or in the final stages of regulatory approval.

1. Amphetamines—At high doses cause release of dopamine from dopaminergic nerve terminals, particular in the neostriatum. At still higher doses, they cause release of 5-hydroxytryptamine (5-HT) and dopamine in the mesolimbic system.

Dextroamphetamine (Dexedrine®)
Methamphetamine (Desoxyn®)
Fenfluramine (Pondimin®)
Diethypropion (Tenuate®)
Mazindol (Mazanor®)
Phentermine (Fastin®)
Benzphetamine (Didrex®)
Phendimetrazine (Phenazine®)
Phenmetrazine (Preludin®)
Chlorphentermine (Pre Sate®)*
Clobenzorex*
Cloforex*
Methylphenidate (Ritalin®)
Pemoline (Cylert®)
Clortermite (Voranil®)*
Dexfenfluramine*
Ethylamphetamine*
Fenethylline*
Fenproporex*
Mefenorex*
Phenatine*
Phenbutrazate*
Prolintane*

Propylhexedrine*
Triflorex*

2. Tricyclic antidepressant and other antidepressants—block the reuptake of serotonin, dopamine, and/or norepinephrine at the neuronal membrane. The degree of potency and selectivity vary greatly among these agents.

Amitriptyline (Elavil®)
Amoxapine (Asendin®)
Bupropion (Wellbutrin®)
Desipramine (Norpramin®)
Doxepin (Sinequan®)
Imiprsmine (Tofranil®)
Nortriptyline (Pamelor®)
Protriptyline (Vivactil®)
Trimipramine (Surmontil®)
Fluoxetine (Prozac®)
Sertraline (Zoloft®)
Paroxetine (Paxil®)
Trazodone (Desyrel®)
Clomipramine (Anafranil®)
Alaproclate*
Amineptine*
Butriptyline*
Cianopramine*
Citalopram*
Clovoxamine*
Dibenzepin*
Dichlofensine*
Dimetacrine*
Dothiepin*
Femoxetine*
Fluvoxamine**
Iprindole*
Lofepramine*
Melitracen*
Minaprine*
Noxiptyline*
Opipramol*
Propizepine*
Quinupramine*
Viloxazine*

3. Monoamine Oxidase (MAO) Inhibitors—block deamination of dopemine and serotonin.

Isocarboxazid (Marplan®)
Phenelzine (Nardil®)
Tranylcypromine (Parnate®)
Selegiline (Deprenyl®)
Clorgyline*
Iproclozide*
Iproniazid
Mebanazine*
Moclobemide*
Nialamide*
Safrazine*
Toloxatone*

4. Dopamine Agonists—immediate metabolic precursor of dopamine in the basal ganglia or release of dopemine from central neurons in the basal ganglia (i.e., nigrostriatal neurons).

Levodopa/carbidopa (Sinemet®)
Amantadine (Symmetrel®)
Bromocriptine (Parlodel®)
Pergolide (Permax®)
Apomorphine
Benserazide*
Lysuride*
Mesulergine*
Lergotrile*
Memantine*
Metergoline*
Piribedil*
GBR12909*—investigational
Tyramine
Tyrosine
Phenylalanine 5. Miscellaneous Buspirone (Buspar®)—appears to act as a mixed agonist/antagonist at both the dopaminergic and serotonin receptors.

Lithium (Eskalith®)—enhances the release of serotonin, especially in the hippocampus and may alter reuptake of catecholamines (i.e., dopamine).

Nicotine (Nicorette®, Habitrol® patch)—stimulates release of norepinephrine and dopamine from brain tissue.

Phencyclidine—inhibits reuptake of dopamine, serotonin, and norepinephrine by synapses.

Marihuana (cannabis)

Lysergic Acid—serotonin agonist.

Reserpine (Ser-Ap-Es®)—inhibit reuptake of dopamine and serotonin, resulting in depletion of stores.

Tryptophan—a precursor of serotonin.

5-hydroxytriptophan—a metabolite of tryptophan, may be administered in doses ranging from 30 to 500 mg per day in single or divided doses.

Oxitriptan*—a precursor of serotonin.

Methylxanthenes generally including

Xanthines and methylxanthines including caffeine, theophylline, Pentoxiphylline and theobromine Ibogaine Thalidomide Supidamide In the above listing * indicates products not available in the United States and **products to be marketed soon by Solvay Pharmaceuticals in the United States.

The preferred agents are fenfluramine and phentermine. Fenfluramine is a racemic mixture of a drug which releases serotonin to the central and peripheral nervous system and inhibits serotonin reuptake into the neuron. Either optical isomer or a racemic mixture may be used. Preferably the mount administered is from 10 to 120 mg/day preferably 80 mg/day in single or preferably divided doses of 40 mg each.

Phentermine is an adrenergic compound structurally related to amphetamines. Such agents typically increase dopamine and noradrenaline concentrations at their respective receptor sites in the brain. Preferably the daily mount administered is 15 to 500 mg, preferably 30–60 mg mg of phentermine, in single or divided doses. A single dose in the morning is preferred. Alternatively 5-hydroxytriptophan may be administered in mounts ranging from 30 to 500 mg in daily or divided doses.

For most treatments the above noted drugs are used in the dosage ranges and mounts indicated in the directions for use and labeling provided by the manufacturer of the product and/or stated in the relevant scientific literature. In particular, see the following sources: Gilman et al., *The Pharmacological Basis of Therapeutics*, 7th ed. New York: Macmillan Publishing Co., 1985; McEvoy GK, ed. *AHFS Drug Information*, Bethesda, MD, American Society of Hospital Pharmacists, Inc., 1993; and Reynolds JE, ed. *Martindale: The Extra Pharmacopoeia*, 29th ed. London, The Pharmaceutical Press, 1989, Although no particular mechanism of action is apparent, it appears that a decrease in serotonin is important in the stress reaction cascade. Since the stress reaction includes a loss of competence in the immune system, the increase of serotonin, especially from a powerful serotonin releaser such as fenfluramine, most likely through the downgrading of the stress reaction, increases the competence of the immune system.

Suitable formulations include those suitable for oral, rectal and parenteral (including subcutaneous, intradermal, intramuscular and intravenous) administration. The formulation may, where appropriate, be conveniently presented in discrete dosage units and may be prepared by any of the methods well known in the art of pharmacy.

The oral route of administration is preferred, desirably in a single dosage unit as appropriate to the dosage regimen. Therapeutic formulations suitable for oral administration in which the carrier is a solid are most preferably presented as unit dose formulations such as boluses, capsules or tablets each containing a predetermined amount of the active ingredients. A tablet may be made by compression or molding, optionally with one or more accessory ingredients. Compressed tablets may be prepared by compressing in a suitable machine the active ingredients in a flee-flowing form such as a powder or granules optionally mixed with a binder, lubricant, inert diluent, lubricating agent, surface-active agent or dispersing agent. Molded tablets may be made by molding active ingredients with an inert liquid diluent. Tablets may be optionally coated and, if uncoated, may optionally be scored. Capsules may be prepared by filling the active ingredients, either alone or in admixture with one or more accessory ingredients, into the capsule shells and then sealing them in the usual manner. Cachets are analogous to capsules in which the active ingredient together with any accessory ingredient(s) is sealed in a rice paper envelope.

Formulations suitable for use in the invention also include dispersible granules, which may for example be suspended in water before administration, or sprinkled on food. The granules may be packaged, e.g. in a sachet. Formulations suitable for oral administration where the carrier is a liquid may be presented as a solution or a suspension in an aqueous liquid or a non-aqueous liquid, or as an oil-in-water liquid emulsion.

Formulations for oral administration include controlled release dosage forms, e.g. tablets where the active ingredients are formulated in on appropriate release-controlling matrix, or are coated with a suitable release-controlling film.

Therapeutic formulations suitable for rectal administration where the carrier is a solid are most preferably presented as unit dose suppositories. Suitable carriers include cocoa butter and other materials commonly used in the art. The suppositories may be conveniently formed by admixture of the active ingredients with the softened or melted carrier(s) followed by chilling and shaping in molds.

Therapeutic formulations suitable for parenteral administration include sterile solutions or suspensions of the active ingredients in aqueous or oleaginous vehicles. Injectable preparations may be adapted for bolus injection or continuous infusion. Such preparations are conveniently presented in unit dose or multi-dose containers which are sealed after introduction of the formulation until required for use. Alternatively, the active ingredient may be in powder form which is constituted with a suitable vehicle, such as sterile, pyrogen-free water, before use.

Also contemplated but less preferred are products formulated as long-acting depot preparations, which may be administered by intramuscular injection or by implantation, e.g. subcutaneously or intramuscularly. Depot preparations may include, for example, suitable polymeric or hydrophobic materials, or ion-exchange resins. Such long-acting formulations are particularly convenient for prophylactic use.

In addition to the above carrier ingredients the therapeutic formulations for the various routes of administration described above may include, as appropriate, one or more additional carrier ingredients such as diluents, buffers flavoring agents, binders, surface active agents, thickeners, lubricants, preservatives (including anti-oxidants) and the like, and substances included for the purpose of rendering the fomulation isotonic with the blood of the intended recipient.

This invention is further explained with reference to the following non-limiting examples.

EXAMPLE 1

A 43 year old registered nurse presented for treatment of idiopathic anaphylaxis. She had previously been diagnosed after an anaphylactic episode three years ago. Since then she had suffered roughly ten episodes a year and had become increasingly refractory to corticosteroids, catecholamines, and antihistamines and was considered to be in the malignant phase of her condition. While the remainder of her anaphylactic triggers were unknown, shellfish ingestion invariably produced shock. Nearly constant asthma was a severe handicap. She was never free of bronchospastic symptoms for more than three straight days over the past three years. She was previously treated unsuccessfully with corticosteroids, catecholamines, and a bevy of antihistamines including ketotifen.

An hour after initiation of treatment consisting of 40 mg. of fenfluramine and 30 mg of phentermine, the patient's wheezing and dyspnea disappeared. Despite the patient's personal decision to halt conventional therapy, she continued to be without symptoms except for mild bronchospasm at three A.M. successfully treated by an increase in the phentermine dose. Eleven days after the initiation of treatment, emboldened by her clinical response, she ate shellfish with no ill-effect. Other than xerostomia, she has suffered no side-effects. The cessation of corticosteroids and the anorectic effect of the fenfluramine/phentermine treatment caused her to decrease her weight from 195 to 165 lbs. in the first two weeks of treatment. Three months into treatment, she has lost a total of 49 lbs. Serum histamine, previously markedly elevated, is now within normal range. She is totally asymptomatic.

EXAMPLE 2

A 33 year old male, HIV positive and advancing towards full blown AIDS, had a CD4+ count of 170. Therapy with 80 mg daily doses of fenfluramine and 30 mg of phentermine was initiated and following 2 days/weeks of this treatment the patient's CD4+ values increased to 480 and other clinical conditions including depression, and anxiety improved.

EXAMPLE 3

A 28 year old male, depressed and craving cocaine was treated with 40 mg of fenfluramine and 30 mg of phentermine in the morning and 40 mg of fenfluramine in the afternoon. At the beginning of treatment the patient's CD4+ level was 530. At the end of 6 weeks therapy the patient's CD4+ level increased to 800 and the patient's craving for cocaine was resolved and depressed state improved.

EXAMPLE 4

An author in his mid 40's presented for weight reduction. Coincident with his severe obesity (343 lbs), he was found to suffer from depression, anxiety, OCD, and psoriasis. After two weeks of therapy (80 mg of fenfluramine and 30 mg of phentermine) he reported total relief of his neurotic symptoms. His nails, previously bitten to the quick, had begun to grow out. His psoriatic lesions were markedly improved. After two months of treatment, he has lost 33 lbs and was continuing to enjoy marked relief from his food craving. His psoriatic lesions were gone.

EXAMPLE 5

A 32 year old unemployed male sought assistance in treating his cocaine, alcohol, and heroin addiction. He had started to drink alcohol at the age of 5 and was alcohol addicted by the age of 15. In the past, he had a narcotic addiction and developed a cocaine addiction ten years ago. Two years ago he was found to be HIV+. His CD4+ count rapidly declined and was at $170/m^3$ prior to treatment.

Before treatment, his SCL psychometric evaluation showed him to be more than three standard deviations above normal in the anxiety, depression, somaticism, hostility, and global severity sub-scales. He was acutely craving cocaine. Within ninety minutes of initial treatment with 40 mg of fenfluramine and 30 mg of phentermine, his cravings and dysphoria ceased. Treatment continued with 80 mg of fenfluramine and 30 mg of phentermine daily. Two weeks later, his SCL was within normal limits. He reported that he felt totally normal without any distress except for a legitimate concern about his finances and his immune status. His CD4+ count increased to $480/mm^3$. He continued to do well for the next four months. There were no AIDS related symptoms. Unfortunately, he was accused of petty larceny and was threatened with incarceration. His phone calls reflected total return of his depression and other stress related dysphoria. His CD4+ cell count dropped to $180/mm^3$. He has been lost to follow up although attempts to reach him continue.

One aspect of my invention includes treating disorders oft he immune system including allergic rhinitis, asthma, idiopathis anaphylaxis and psoriasis. Another aspect of my invention includes the treatment of disorders of the immune system selected from anaphylaxis to specific allergen, exercise induced anaphylaxis, chronic hepatitis C, chronic hepatitis B, Crohn's Disease, ulcerative colitis, rheumatoid arthritis, psoriatic arthritis,, Reiter's Syndrome, scleroderma and lupus erythematosus

What is claimed is:

1. A method of treating a disorder to the immune system selected from the group consisting of fibromyalgia and chronic fatigue syndrome comprising administering to a patient in need of same an effective amount of at least one serotonin agonist and at least one dopamine agonist wherein the combination of the serotonin agonist and the dopamine agonist are present in an amount effective to treat the patient's condition.

2. The method of claim 1 in which the serotonin agonist and dopamine agonist are administered simultaneously.

3. The method of claim 1 in which the serotonin agonist and dopamine agonist are intimately mixed together and administered in a single dosage unit.

4. The method of claim 1 in which the serotonin, in agonist is fenfluramine and the dopamine agonist is phentermine.

5. The method of claim 4 in which 10 to 90 mg of fenfluramine and 15 to 500 mg of phentermine are administered to the patient per day in single or divided doses.

6. The method of claim 1 in which the immune disorder is fibromyalgia.

7. The method of claim 1 in which the immune disorder is chronic fatigue syndrome.

8. A method of improving vector gene therapy by reducing an immune response to a gene therapy vector comprising administering to a patient in need of same an effective amount of at least one serotonin agonist and at least one dopamine agonist wherein the combination of the serotonin agonist and the dopamine agonist are present in an amount effective to treat the patient's condition.

9. The method of claim 8 wherein the vector is an adenoviral vector.

10. A method of treating a disorder to the immune system selected from the group consisting of fibromyalgia and chronic fatigue syndrome comprising administering to a patient in need of same 10 to 90 mg of fenfluramine and 15 to 160 mg of phentermine per day in single or divided doses wherein the combination of the serotonin agonist and the dopamine agonist is present in an amount effective to treat the patient's condition.

* * * * *